United States Patent [19]

Faler

[11] 4,375,567
[45] Mar. 1, 1983

[54] METHOD FOR MAKING BISPHENOL

[75] Inventor: Gary R. Faler, Scotia, N.Y.

[73] Assignee: General Electric Company, Schenectady, N.Y.

[21] Appl. No.: 294,659

[22] Filed: Aug. 21, 1981

[51] Int. Cl.$^3$ ............................................. C07C 39/16
[52] U.S. Cl. .................................... 568/727; 568/724; 568/728
[58] Field of Search .................... 568/727, 728, 724

[56] References Cited

U.S. PATENT DOCUMENTS

| | | | |
|---|---|---|---|
| 3,049,569 | 8/1962 | Apel et al. | 568/724 |
| 3,153,001 | 10/1964 | Apel et al. | 521/33 |
| 3,221,061 | 11/1965 | Grover et al. | 568/724 |
| 3,843,566 | 10/1974 | Barrett | 521/33 |
| 4,191,843 | 3/1980 | Kwantes et al. | 568/727 |
| 4,256,840 | 3/1981 | Meitzner et al. | 521/33 |
| 4,263,407 | 4/1981 | Reed | 521/33 |
| 4,308,404 | 12/1981 | Kwantes et al. | 568/727 |
| 4,308,405 | 12/1981 | Kwantes et al. | 568/727 |

FOREIGN PATENT DOCUMENTS 2048661  4/1972  Fed. Rep. of Germany ...... 568/724

*Primary Examiner*—Werren B. Lone
*Attorney, Agent, or Firm*—William A. Teoli; James C. Davis, Jr.; James Magee, Jr.

[57] ABSTRACT

A method is provided for making bisphenol-A based on the condensation of acetone and phenol in the presence of an ion-exchange resin. Improved yields of 2,2-bis(4-hydroxyphenyl)propane is achieved by recycling bisphenol-A reaction mixture containing significant amounts of 2,4'-dihydroxy-2,2-diphenyl propane based on the use of a macroreticular ion-exchange resin.

2 Claims, 1 Drawing Figure

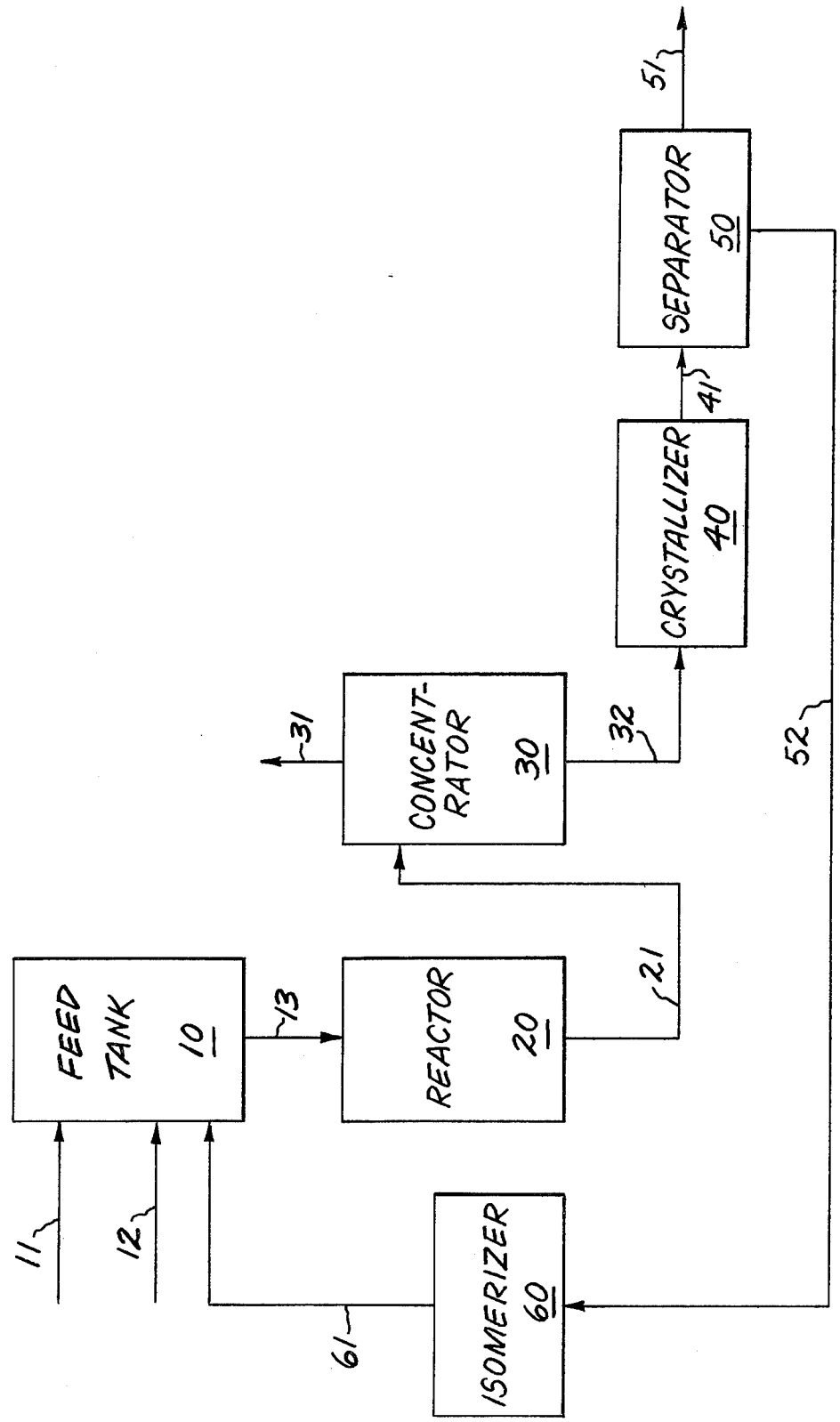

METHOD FOR MAKING BISPHENOL

CROSS REFERENCE TO RELATED APPLICATIONS

Reference is made to copending applications Ser. No. 226,271, filed Jan. 19, 1981, for Method for Salvaging Bisphenol Values, of Ashok Mendiratta, assigned to the same assignee as the present invention.

BACKGROUND OF THE INVENTION

As shown by F. N. Apel et al, U.S. Pat. Nos. 3,049,568, 3,049,569 and 3,153,001 and A. R. Grover et al, U.S. Pat. No. 3,221,061, ion-exchange resins have been found to be useful for effecting the condensation of acetone and phenol for making 2,2-bis-(4-hydroxyphenyl)propane of the formula,

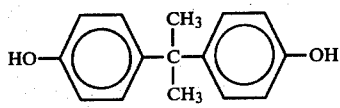

commonly referred to as "bisphenol-A" and referenced to hereinafter as the "4,4'-isomer". Experience has shown that, during the condensation reaction of acetone and phenol, in the presence of an ion-exchange catalyst, significant amounts of 2,4'-dihydroxy-2,2-diphenyl propane can be formed having the formula,

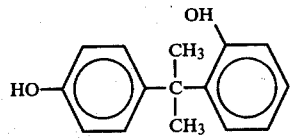

referred to hereinafter as the 2,4-isomer.

When strong mineral acids, such as hydrochloric acid, are employed as catalysts in the condensation reaction, the 2,4-isomer can rearrange to the desired 4,4'-isomer under the reaction conditions. However, these reaction conditions result in the formation of significant amounts of tars which are difficult to salvage. These tars result in the formation of complex color forming aromatics which can adversely affect the utility of the desired 2,2-bis(4-hydroxyphenyl)propane monomer. As a result, efforts are constantly being sought to improve the effectiveness of ion-exchange catalysts for the formation of bisphenol-A in place of mineral acid catalyst, while minimizing the production of undesirable amounts of the 2,4'-dihydroxy-2,2-diphenyl propane, which can impair the purity of the desired bisphenol-A monomer.

One solution to the "isomer" problem when using an ion-exchange catalyst is to recycle the reaction by-products effluent from the bisphenol-A reaction stream after a concentration and recrystallization step. The by-product stream is then recycled to an isomerization zone to convert 2,4'-dihydroxy-2,2-diphenyl propane, hereinafter referred to as the "2,4'-isomer" to bisphenol-A, or the "4,4'-isomer" which can be further recycled to a feed tank along with makeup acetone and phenol and thereafter introducing the resulting isomerized mixture along with makeup feed to the reactor. Although in theory, the use of an isomerization step for the by-product feed which can be recycled to the reactor has achieved some degree of success as measured by improved rates of bisphenol-A production, the effectiveness of such isomerization procedure has often not achieved the degree of success desired. Improved isomerization procedures to convert the 2,4'-isomer to the 4,4'-isomer and accordingly more effective techniques to improve the rate of formation of bisphenol-A are constantly being sought.

As taught by Reed, U.S. Pat. No. 4,263,407, the term "macroreticular" as opposed to "microreticular" means porous adsorbance in which the pores are larger than atomic distances and are not part of the polymer structure per se. Rather, the pores are microscopic channels resulting from the squeezing out of an organic precipitant from a copolymer mass. As a consequence, the pore structure is not dependent upon environment and therefore is retained despite contact with various concentrations of electrolyte, solvent and exchangable ions.

In microreticular resins (gel-type) the pores are not really pores at all because they are extremely small, usually below 30 A in diameter and will disappear from the polymer structure when the polymer is dry. The microreticular gel resin has a continuous polymer phase while the macroreticular resin is clearly shown to consist of conglomerates of granularly packed macrospheres with both a continuous polymer phase and a continuous void phase. Thus the expression "porous" as used herein refers to channels or openings between conglomerates of minute spherical particles.

The present invention is based on the discovery that macroreticular cation-exchange catalyst have been found to be particularly useful for directly converting the 2,4'-isomer to the 4,4'-isomer. Accordingly, an improved procedure for isomerizing the 2,4'-isomer to the 4,4'-isomer has now been found.

STATEMENT OF THE INVENTION

There is provided by the present invention a continuous process for making bisphenol-A by condensing phenol and acetone in the presence of an ion-exchange catalyst, resulting in the production of effluent comprising 2,2-bis(4-hydroxyphenyl)propane and a contaminating amount of 2,4'-dihydroxy-2,2-diphenyl propane, whereby said effluent is transported to a bisphenol-A concentrator, a crystallizer and a solid/liquid separator to effect the separation of bisphenol-A from its reaction by-product and starting reactants which are recycled to an isomerization zone containing an ion-exchange catalyst to effect the conversion of said 2,4'-dihydroxy-2,2-diphenyl propane to 2,2-bis(4-hydroxyphenyl)propane which is recycled to a bisphenol feed tank, the improvement which comprises, utilizing as the ion-exchange resin in the isomerization zone, a macroreticular cationic-exchange catalyst whereby improved conversion of 2,4'-dihydroxy-2,2-diphenyl propane to 2,2-bis-(4-hydroxyphenyl)propane is achieved.

In order that those skilled in the art will be better able to practice the invention, reference is made to the drawing.

There is shown in the schematic a feed tank which conveys reaction mixture to a reactor which is joined to a concentrator and the bottoms of the concentrator is fed into a recrystallizer and a separator from which substantially pure 4,4'-isomer of bisphenol-A is collected and which recycles isomer feed to an isomerizer.

More particularly, there is shown at 10 a feed tank having feed ports at 11 and 12 allowing for the introduction of acetone and phenol and recycled isomer feed at 61. Reactant mixture is fed to the reactor at 20 through line 13. Reaction mixture is directed through lines 21 to concentrator 30 which separates unreacted phenol and acetone at 31 for recycle and bisphenol-A reaction stream at 32. The bisphenol-A reaction stream is led into a crystallizer at 40 to produce a solid and liquid mixture which is fed to the separator at 50. The bisphenol-A solids are fed at 51 to a melter and evaporator not shown, while the liquid by products are fed to the isomerizer at 60 through line 52. The isomerized mixture is then recycled to the feed tank at 10 through line 61.

In the practice of the invention, a mixture of acetone and phenol are fed into the feed tank which also has ports, allowing for the entry of feed from the isomerization zone and recycled feed from the concentrator. The rates at which the makeup acetone and phenol along with the recycled feed and isomerization feed are maintained to allow for the production of a mixture which is fed into the reactor having the proper material balance to achieve optimum rate of production of the 4,4'-isomer. The "total feed mixture" is heated prior to its introduction into the reactor. The reactor can be equipped with an ion-exchange bed, for example, a sulfonated insoluble polystyrene, such as Dowex 50W-4 modified with a mercaptan. The residence time can vary widely, and typically can be 60 minutes more or less.

The acetone-phenol reaction is preferably carried out utilizing a stoichiometric excess of phenol. Preferably a temperature in the range of about 55° C. to 125° C. is preferred in order to avoid plugging of the reactor.

Reaction is initiated by heating the phenol and acetone under substantially anhydrous conditions, that is less than 2% by weight of water and preferably less than 0.2% water content by weight, to reaction temperature. The reactants are passed through a fixed porous bed of ion-exchange resin, at a slight pressure to maintain adequate flow, although gravity pressure is also found to be satisfactory. The effluent is then passed into a concentrator where all of the water, phenol and acetone are removed as an overhead fraction. The bottoms from the concentrator are then passed to a crystallization zone, where crystallization is carried out by chilling the bottoms from the concentrator to a temperature between about 37° C. to 95° C. An adduct of phenol and the 2,2-isomer separates out as crystals which can be separated from the mother liquor by centrifuging, filtration, etc. The crystals can then be washed with phenol and the washings along with the mother liquor can then be recycled to the isomerization zone.

The isomerization zone consists of a bed of macroreticular ion-exchange catalysts as distinguished from the reactor which is a fixed bed of either microreticular or macroreticular ion-exchange resin. The mother liquor and the washings from the crystallizer are then allowed to pass through the macroreticular ion-exchange resin which can be at a temperature of from 60° C. to 120° C. for a period of time sufficient to effect rearrangement of the 2,4'-isomer to the 4,4'-isomer depending upon such factors as the feed rate, the size of the bed, etc. The isomerized feed is then fed back to the feed tank along with the makeup acetone and phenol for reuse in the reactor.

In order that those skilled in the art will be better able to practice the present invention, the following examples are given by way of illustration and not by way of limitation. All parts are by weight.

EXAMPLE 1

A rate study was made to determine the effectiveness of typical microreticular cation-exchange catalysts, such as Amberlite-118 of the Rohm and Haas Company, of Philadelphia, PA and Dowex 50WX2 of Dow Chemical Company, Midland, Mich., both sulfonated insoluble polystyrene resins to isomerize 2,4'-dihydroxy-2,2-diphenyl propane or "2,4'-isomer" to 2,2-bis(4-hydroxyphenyl)propane, or "BPA".

The microreticular resins were then compared in the same manner to equivalent weights of Amberlyst-15 and Amberlyst-XN-1010, commercially available macroreticular resins of Rohm and Haas Company. The following procedure was used to determine the first order rate constant of isomerization using the various ion-exchange resins.

There was added 5 parts of activated ion-exchange resin and 0.5 part of 2,4'-dihydroxy-2,2-diphenylpropane to 20 parts of dry phenol. The mixture was placed in a preheated oil bath at 70° C. and small aliquats were withdrawn at specific time intervals, diluted with 20 parts of acetonitrile, followed by high pressure liquid chromatography analysis. The results of the various ion-exchange catalyst rate studies were plotted on a natural log scale and are shown in the following table:

TABLE I

| Catalyst | k (min$^{-1}$ met$^{-1}$) | k$_{rel}$ |
|---|---|---|
| Amberlit-118[a] | 7.58 × 10$^{-5}$ | 0.052 |
| Dowex 50WX2[a] | 72.2 × 10$^{-5}$ | 0.402 |
| Amberlyst-15[b] | 80.9 × 10$^{-5}$ | 0.552 |
| Amberlyst XN-1010[b] | 147. × 10$^{-5}$ | 1.0 |
| Amberlyst XN-1010[b] + 0.5% H$_2$O | 118. × 10$^{-5}$ | 0.804 |
| Amberlyst XN-1010[b] + 1.0% H$_2$O | 74.3 × 10$^{-5}$ | 0.508 |
| Amberlyst XN-1010[b] + 2.0% H$_2$O | 40.8 × 10$^{-5}$ | 0.279 |
| Amberlyst XN-1010[b] + 3.0% H$_2$O | 20.0 × 10$^{-5}$ | 0.136 |

[a]This catalyst is microreticular
[b]This catalyst is macroreticular

The above results show that macroreticular resins as illustrated by Amberlyst-15 and Amberlyst XN-1010 are more effective as isomerization catalysts for converting the 2,4'-isomer to the 4,4'-isomer than Amberlite-118 or Dowex 50WX2. In addition, the above results also show that the isomerization rate is effected by trace amounts of water.

EXAMPLE 2

As shown in the copending application Ser. No. 226,271 of A. R. Mendiratta, filed Jan. 19, 1981, and assigned to the same assignee as the present invention, a glass ion-exchange resin column was charged with 45 parts of macroreticular, sulfonated polystyrenedivinylbenzene ion-exchange resin beads of the Rohm & Haas Company having a mesh size of 28-48 and furnished commercially under the trademark Amberlyst XN-1010. The resin bed was washed with 4 bed volumes of 80:20 (by weight) phenol-water solution. This was followed by 3 bed volumes of dry phenol wash.

An isomer stream consisting of 80.4% of phenol, 8% of bisphenol-A, 3.2% o,p-bisphenol-A and 8.4% of various by-products by weight was fed into the above ion-exchange resin bed. A total of 18 bed volumes of the isomer feed mixture was passed through the column. There was obtained an effluent isomer stream having the following composition by weight: phenl 79.9%; bisphenol-A 8.9%; o,p-bisphenol-A 2.9%; and other products 8.3%.

The above results show that the macroreticular resin of the present invention had a noticable influence on the composition of the isomer stream with respect to reducing the 2,4-isomer of bisphenol-A.

Although the above examples are directed to only a few of the very many variables of the method of the present invention, it should be understood that the present invention is directed to a much broader class of macroreticular resins and to procedures and conditions for separating and recovering the bisphenol-A in the practice of the method of the present invention.

What I claim as new and desire to secure by Letters Patent of the United States is:

1. In a continuous process for making bisphenol by condensing phenol and acetone in the presence of an ion-exchange catalyst resulting in the production of effluent comprising 2,2-bis(4-hydroxyphenyl)propane and a contaminating amount of 2,4'-dihydroxy-2,2-diphenyl propane, whereby said effluent is transported to a bisphenol-A concentrator, a crystallizer and a solid/liquid separator to effect the separation of bisphenol-A from its reaction by-product and starting reactants which are recycled to an isomerization zone containing an ion-exchange catalyst to effect the conversion of said 2,4'-dihydroxy-2,2-diphenyl propane to 4,4'-bis(4-hydroxyphenyl)propane which is recyled to a bisphenol feed tank, the improvement which comprises, utilizing as the ion-exchange resin in the isomerization zone a macroreticular cationic-exchange catalyst whereby improved conversion of 2,4'-dihydroxy-2,2-diphenyl propane to 2,2-bis-(4-hydroxyphenyl)propane is achieved.

2. A method in accordance with claim 1, where the macroreticular cationic-exchange catalyst is a sulfonated polystyrene-divinylbenzene ion-exchange resin.

* * * * *